United States Patent [19]

Boettger et al.

[11] Patent Number: 4,567,303

[45] Date of Patent: Jan. 28, 1986

[54] PROCESS AND APPARATUS FOR PREPARING OR REACTING ALKANOLAMINES

[75] Inventors: Guenter Boettger, Bad Durkheim; Hans Hammer, Mannheim; Otto Hertel, Ludwigshafen; Gerhard Jeschek, Gruenstadt; Herbert Mueller, Frankenthal; Emil Scharf, Ludwigshafen; Willibald Schoenleben, Heidelberg, all of Fed. Rep. of Germany

[73] Assignee: BASF Aktiengesellschaft, Fed. Rep. of Germany

[21] Appl. No.: 638,522

[22] Filed: Aug. 6, 1984

Related U.S. Application Data

[60] Continuation of Ser. No. 381,721, May 24, 1982, which is a division of Ser. No. 242,258, Mar. 10, 1981.

[30] Foreign Application Priority Data

Mar. 15, 1980 [DE] Fed. Rep. of Germany ....... 3010105

[51] Int. Cl.$^4$ ............................................. C07C 65/01
[52] U.S. Cl. .................................... 564/475; 564/478
[58] Field of Search ................................ 564/475, 478

[56] References Cited

U.S. PATENT DOCUMENTS

| | | | |
|---|---|---|---|
| 3,459,671 | 8/1969 | Marklow et al. | 564/478 X |
| 4,036,881 | 7/1977 | Brennan et al. | 564/475 X |
| 4,059,440 | 11/1977 | Takemura et al. | 564/478 X |
| 4,078,003 | 3/1978 | Feichtinger et al. | 564/475 X |

OTHER PUBLICATIONS

Rothenberg, "Specialty Steels", Noyes Data Co., Parkridge, N.J., pp. 137–138, 1977.

*Primary Examiner*—Paul F. Shaver
*Attorney, Agent, or Firm*—Keil & Weinkauf

[57] ABSTRACT

In preparing or reacting alkanolamines, especially at high temperatures, the use of substantially nickel-free alloy steels prevents corrosion and discoloration.

7 Claims, No Drawings

PROCESS AND APPARATUS FOR PREPARING OR REACTING ALKANOLAMINES

This application is a continuation of application Ser. No. 381,721, filed on May 24, 1982, which was a divisional of application Ser. No. 242,258 filed Mar. 10, 1981.

The present invention relates to a process for preparing colorless alkanolamines, which do not discolor even on storage, from ammonia or reactive amines and alkylene oxides, their further reaction with ammonia to give alkylenediamines or alkylenepolyamines, their purification, and an apparatus for preparing or reacting alkanolamines.

Alkanolamines, especially diethanolamine and triethanolamine, which are colorless per se, as a rule show, as industrial products, yellowish to brownish discoloration attributable to unknown impurities. On storage, the color usually deepens and thus makes them useless for certain typical applications, for example the preparation of cosmetics, pharmaceutical products and auxiliaries containing surfactants.

This phenomenon is even more troublesome when the amines are converted to salts, as this causes the color to change to brown or blue, generally even darker, hues. Furthermore, once discoloration has occurred, it can virtually no longer be removed, especially since the distillation of alkanolamines is known to require high temperatures and an expensive separation.

The same problem also arises on further conversion of the alkanolamines, i.e. the preparation or processing of aliphatic or cycloaliphatic diamines and polyamines which may or may not contain alcoholic OH groups. Examples include the reaction products of alkanolamines with ammonia, i.e. ethylenediamine and propylenediamine, and the byproducts arising from the diamine synthesis, i.e., for example, diethylenetriamine, triethylenetetramine, piperazine, N-(2-aminoethyl)-piperazine, N-(2-hydroxyethyl)-piperazine and N-(2-aminoethyl)-ethanolamine.

The fact that the preparation or reaction of the alkanolamines is frequently accompanied by severe corrosion of the equipment used gives a certain indication of the origin of the impurities. For the industrialpreparation and processing of the compounds mentioned, the apparatus used is always made from conventional chrome-nickel (stainless) steels, for example No. 1.4541, 1.4550 or 1.4571. These materials show little tendency to develop stress corrosion, afford good heat transfer and permit the use of superatmospheric pressure or of reduced pressure at elevated temperatures, such pressures being necessary for the synthesis and for working up by distillation. Other conventional "stainless" steels are not used in chemical engineering equipment because they cannot be welded or tend to develop stress corrosion under pressure. Though the pressure-resistant stainless steels used in chemical plant, which are almost exclusively austenitic chromium-nickel steels (see classification in L. Piatti, Werkstoffe der chemischen Technik, "Grundlagen der Chemischen Technik" series, vol. 3, pp. 264 to 268), are regarded as having good corrosion resistance to amines, contact with the above compounds results in substantial local corrosion. Internal fitments in columns and reactors are particularly prone to this. ON the other hand, for example, even severely discolored alkanolamines do not contain any significant amounts of heavy metals.

The literature gives no indication of the origin of the discolorations.

Since the use of ceramic or glass components is virtually ruled out because of the requisite pressures and the strongly alkaline nature of the reaction mixtures, attempts have hitherto been made to minimize the problems by means of additives; however, hitherto, according to German Published Application DAS 2,810,185, it has only been possible to control discoloratons, to a certain degree, by adding phosphorous acid or the like. Sufficient suppression of corrosion was not achievable by these means.

It is an object of the present invention to avoid the discoloration of reaction products in the reaction sequence ammonia→alkanolamines→alkylenediamines or alkylenepolyamines, and to counteract corrosion phenomena.

We have found that this object is achieved and that corrosion and discolorations can be avoided in the said processes if instead of conventional nickel-alloyed stainless steels, i.e. steels whose corrosion resistance is due to alloying of nickel, steels which are substantially nickel-free are used as the material of construction of the apparatus; frequently, a substantial improvement in existing apparatus is achievable by merely replacing individual components, on which corrosion has occurred, by components made of low-nickel or nickel-free material. The use of nickel-free materials is particularly to be recommended in internal fitments such as packings, heat exchange tubes and, generally, those components which are exposed to severe thermal or mechanical conditions (for example a high flow rate). Preferred steels are low-carbon (<0.0125%) ferritic steels which contain, for example, from 17 to 19% chromium, from 1.75 to 2.5% molybdenum, up to 0.5% manganese, up to 1% silicon and up to 0.025% nitrogen, the nickel content usually being less than 0.5%.

This result is surprising since the conventional preliminary laboratory-scale corrosion testing in order to select a suitable material for the apparatus, in the case of the alkanolamines suggests the use of conventional nickel-containing alloy steels and rules out nickel-free steels. Evidently, a plant in industrial operation behaves differently from models operated for only a limited period. In view of the results of corrosion tests a certain prejudice therefore had to be overcome in order to arrive at the invention.

Other references, e.g. Kirk-Othmer, Encyclopedia of Chemical Technology, 3rd Ed., Vol. 1, p. 955, which suggests the use of stainless steel to avoid discoloration of alkanolamines, and Corrosion Data Survey, Metals Section, N. E. Hammer, National Association of Corrosion Engineers, Houston, Tex., U.S.A., p. 184 which mentions only slight corrosion even with hot aqueous triethanolamine solutions, would seem to militate against any connection between the use of stainless steel and corrosion by alkanolamines. There is certainly nothing to suggest that the use of specific materials is essential. An example of an essentially nickel-free alloy steel is material No. 1.4521 (1803 MoT). The apparatus can consist completely or only partially, for example at conventionally corrosion-prone points, of such material, or can be lined with such material. The use of nickel-free steels is to be recommended particularly for parts of apparatus which are exposed to severe thermal and mechanical conditions, for example reactors, vaporizers, heat exchangers, packings and trays in distillation columns.

The invention is applicable wherever alkanolamines and especially ethanolamines arise as starting materials or products in heated reaction mixtures, i.e. in the actual preparation of the alkanolamines, their separation (by distillation) and their further reactions, as well as processes in which alkanolamines perform essentially physical functions, as in gas scrubbing ($CO_2$ scrubbing). The apparatus suitable for the preparation of ethanolamines is frequently also suitable for their further conversion and for the preparation and further conversion of higher alkanolamines (for example propanolamines), espcially in processes which are carried out under pressure.

EXAMPLE 1

Aqueous ammonia was reacted with ethylene oxide at 120°-140° C. and a pressure bar in an industrial plant, wherein the reactor consisted of conventional steel and the working-up section partly of conventional steel and partly of conentional chromium-nickel steel (V2A).

In the distillation section, temperatures of up to 180° C. were encountered, whilst the pressure was reduced stepwise from 20 bar to 0.6 mbar.

According to the products obtained by distillation, the reaction gave 60% of monoethanolamine (MEA), 30% of diethanolamine (DEA) and 10% of triethanolamine (TEA).

The annual erosion of material was from 1 mm (normal steel) to 0.5 mm (alloy steel).

The plant was refitted by replacing about 1,000 m² of packings and 400 m² of heat exchangers (tube bundles) made of V2A steel by those made of Cr-steel 1803 Mo, T.

In addition, the connecting pipes, made of normal steel, of the vaporizers in the ammonia distillation system were replaced by tubes made of a low-Ni steel, 1.4462.

The operating data remained unchanged. In the replaced parts, no corrosive erosion was found after a period of observation of 1 year.

The color numbers (determined by the APHA method) of the products before and after fitting the new parts of the plant are shown in Table 1 below.

The same products were furthermore reacted with acetic acid, and the color numbers again determined (Table 2, APHA method).

TABLE 1

| | APHA color numbers | | | |
|---|---|---|---|---|
| | Before replacement | | After replacement | |
| Product | Fresh products | Products stored for 3 months | Fresh products | Products stored for 3 months |
| MEA | 11.1 | 26.8 | 1.5 | 3.1 |
| DEA | 15.8 | 105.5 | 2.5 | 4.8 |
| TEA | 82.8 | about 350 | 5.7 | 12.5 |

TABLE 2

| | APHA color numbers | | | |
|---|---|---|---|---|
| MEA | 16.3 | 32.7 | 3.1 | 5.6 |
| DEA | 32.6 | 78.1 | 4.2 | 7.1 |
| TEA | deep blue (—) | blackish blue (—) | 20.3 | 25 |

EXAMPLE 2

300 g portions of a technical-grade polyamine were heated, with stirring, for 4 hours in the presence of 30 g of steel filings of a given type. After cooling and filtering, the quality of the products was examined. The results are shown in the Table below, which demonstrates the superiority of the nickel-free steel.

| Material | Steel | Temperature °C. | Color on iodine scale | Determination of distillation residue |
|---|---|---|---|---|
| N—(2-Aminoethyl)-ethanolamine | 1.4550 (V2A; (10.5% of Ni) | 238 | 120 | 0.80% |
| | 1.4521 1802 MoT; (virtually Ni-free) | 238 | 10 | 0.35% |
| N—(2-Hydroxyethyl)-piperazine | 1.4550 | 241 | 15 | 0.40% |
| | 1.4521 | 241 | 7 | 0.25% |

EXAMPLE 3

The reaction of ethanolamine with ammonia to give ethylenediamine results in a product mixture, from which the low-boiling ethylenediamine and piperazine are distilled. The high-boilers which remain and which principally consist of ethanolamine, diethylenetriamine and N-(2-aminoethyl)-ethanolamine, are further separated by distillation in steel apparatus. Nickel-free steel is more suitable for this purpose than is conventional nickel-containing steel, as shown by the experiment below.

300 g of a model mixture of diethylenetriamine, N-(2-aminoethyl)-ethanolamine and ethanolamine were stirred for 24 hours at 170° C. with nickel-containing steel filings and with nickel-free steel filings. The product quality was then found to be the following:

| Type of steel | Color on iodine scale | Determination of distillation residue |
|---|---|---|
| 1.4541 (V2A) (10.5% of Ni) | 15 | 1.5% |
| 1.4521 (virtually Ni-free) | 7 | 0.2% |

We claim:

1. A process for preparing colorless alkanolamines and/or alkylenediamines which comprises thermally reacting ammonia or a reactive amine and an alkylene oxide or alkanolamine in a reactor in which the corrosion-sensitive parts of the reactor are made of substantially nickel-free stainless steel.

2. The process of claim 1, wherein a corrosion-resistant ferritic steel containing less than 0.5% of nickel and/or less than 0.025% carbon is used.

3. The process of claim 1, wherein a substantially nickel-free material is used at specific points, especially at points which normally suffer corrosion.

4. The process of claim 1, wherein the alkylene oxide used is ethylene oxide or propylene oxide.

5. A process for separating by distillation the reaction products of a reaction mixture containing ammonia or a reactive amine and an alkylene oxide or alkanolamine which comprises heating the mixture in an apparatus in which the corrosion-sensitive parts are made of substantially nickel-free stainless steel.

6. The process of claim 5 wherein the corrosion-sensitive parts are made of a corrosion-resistant ferritic steel containing less than 0.5% of nickel and/or less than 0.025% carbon.

7. The process of claim 5 wherein the corrosion-sensitive parts are made of a substantially nickel-free material.

* * * * *